US008440725B2

(12) United States Patent
Beilfuss et al.

(10) Patent No.: US 8,440,725 B2
(45) Date of Patent: May 14, 2013

(54) SYNERGISTIC PREPARATIONS BASED ON MIXTURES OF GLYCEROL ETHER WITH AROMATIC ALCOHOL FOR CONTROLLING MYCOBACTERIA

(75) Inventors: Wolfgang Beilfuss, Hamburg (DE); Ralf Gradtke, Tornesch (DE); Wolfgang Siegert, Ellerau (DE); Michael Mohr, Kaltenkirchen (DE); Klaus Weber, Hamburg (DE)

(73) Assignee: Air Liquide Sante (International), Paris (FR)

( * ) Notice: Subject to any disclaimer, the term of this patent is extended or adjusted under 35 U.S.C. 154(b) by 0 days.

(21) Appl. No.: 12/828,713

(22) Filed: Jul. 1, 2010

(65) Prior Publication Data

US 2010/0331426 A1 Dec. 30, 2010

Related U.S. Application Data

(62) Division of application No. 10/445,715, filed on May 27, 2003, now abandoned.

(30) Foreign Application Priority Data

Jun. 5, 2002 (DE) .................................. 102 24 979

(51) Int. Cl.
*A61K 31/045* (2006.01)
(52) U.S. Cl.
USPC ........................................... 514/730; 514/738

(58) Field of Classification Search ................... 514/730, 514/738
See application file for complete search history.

(56) References Cited

U.S. PATENT DOCUMENTS

| 5,185,145 | A | 2/1993 | Eggensperger et al. |
| 5,516,510 | A | 5/1996 | Beilfuss et al. |
| 5,539,001 | A | 7/1996 | Waldmann-Laue et al. |
| 5,591,442 | A | 1/1997 | Diehl et al. |
| 5,646,105 | A | 7/1997 | Hachmann et al. |
| 6,376,547 | B1 | 4/2002 | Behrends et al. |

FOREIGN PATENT DOCUMENTS

| DE | 4026756 | 2/1992 |
| DE | 4124664 | 1/1993 |
| DE | 4140473 | 6/1993 |
| DE | 4240674 | 3/1994 |
| DE | 19801821 | 7/1999 |
| DE | 10025124 | 11/2001 |
| EP | 0551975 | 7/1993 |
| EP | 0599433 | 6/1994 |
| EP | 1157687 | 11/2001 |

OTHER PUBLICATIONS

Goodman & Gilman's The Pharmacological Basis of Therapeutics, tenth edition, 2001; p. 1274—Table 1.
European Search Report to EP 03 29 1094, Jul. 31, 2003.

*Primary Examiner* — Renee Claytor
(74) *Attorney, Agent, or Firm* — Young & Thompson

(57) ABSTRACT

Disinfectant which has activity towards mycobacteria and has (a) 1-(2-ethylhexyl} glycerol ether and (b) one or more aromatic alcohols group including aryloxyalkanols, ethers and arylalkanols.

1 Claim, No Drawings

SYNERGISTIC PREPARATIONS BASED ON MIXTURES OF GLYCEROL ETHER WITH AROMATIC ALCOHOL FOR CONTROLLING MYCOBACTERIA

CROSS REFERENCE TO RELATED APPLICATIONS

This application is a divisional of application Ser. No. 10/445,715 filed on May 27, 2003, which claims priority to German Application No. 102 24 979.2 filed on Jun. 5, 2002. The entire contents of each of the above-identified applications are hereby incorporated by reference.

BACKGROUND

The present invention relates to a disinfectant and the use of the disinfectant for controlling mycobacteria.

*Mycobacteria* are comparatively difficult to inactivate by biocidal active compounds. Because of their waxy cell wall they are among the most chemically resistant pathogens. Chemicals which have proved sufficiently active are phenols, aldehydes, oxidizing substances such as active oxygen compounds or halogens, and lower alcohols (such as ethanol and propanols). Thus, for example, a modern aldehyde-free disinfectant for manual disinfection of instruments comprises the following active compounds and constituents: 10 to 20% by weight of quaternary ammonium compounds, 5 to 15% by weight of phenoxypropanols, 3 to 10% by weight of aminoalkyl-glycines, nonionic surfactants, anticorrosion agents, pH regulators, fragrances and colourings. An aldehydebased instrument disinfectant comprises 5 to 15% by weight of glutaraldehyde, 7 to 11% by weight of formaldehyde, 2 to 6% by weight of quaternary ammonium compound, nonionic surfactants, pH regulators, fragrances and colourings.

However, these known compositions are frequently aggressive towards the materials to which they are applied, for example parts made of plastic (for example seals of medical instruments) are attacked by these compositions. The use of these biocides can, in addition, on contact with human skin lead to allergies or sensitization. In particular biocides having a strongly electrophilic character (for example isothiazolones, organohalogen compounds) are increasingly becoming the subject of public debate as preservatives and disinfectants and their use is becoming restrictively regulated by legislators. On the other hand, compositions which act less aggressively to the materials or skin, are frequently not sufficiently active towards mycobacteria.

In addition, lower alcohols are only active when used at high concentration and, moreover, have excessive volatility. Phenols, owing to inadequate bio-degradability, have a low acceptance. Active oxygen compounds such as peracetic acid are also used, but because of the pungent odour and the corrosive properties are undesirable. Aldehydes such as formaldehyde or glutardialdehyde are not acceptable owing to toxicological properties and for odour reasons. Amines such as N,N'-bis(3-aminopropyl)lauryl-amine give the mycobactericidal formulations containing this active compound an elevated pH which leads to an increased hazard in skin and material compatibility. Of the tuberculocidally active aromatic alcohols such as phenoxypropanols, significantly greater amounts must be used in order to achieve a corresponding action, which again leads to an increased hazard in material compatibility. Furthermore, N,N'-substituted glycine derivatives have been described as mycobactericidal active compounds (see DE-A-19801821), but these active compounds have a tendency to develop foam, which is undesirable for many applications.

There is therefore a desire for mycobacteria-controlling compositions which do not have the said disadvantages, or do not have the disadvantages to this extent, and are more compatible for humans (especially human skin) and environment. The compositions are to successfully inactivate mycobacteria and are not to act aggressively towards the materials to which they are applied.

The use of glycerol monoalkyl ethers in dermatological compositions is known.

DE-C-42 40 674 discloses that glycerol monoalkyl ethers of the formula R—O—$CH_2$—CHOH—$CH_2OH$ have a deodorizing action. Moreover, a combination of 0.15% by weight of phenoxyethanol with 0.135% by weight of 1-(2-ethylhexyl) glycerol ether is described which comprises, in addition, 40% by weight of ethanol and 0.015% of dibromodicyanobutane.

DE-A-40 26 756 relates to preservatives which comprise, as synergistic active compounds, a mixture of a) an organic acid, b) a monophenyl glycol ether and c) a guanidine derivative. Examples 13 and 14 are concentrates containing more than 60% by weight of phenoxyethanol and 15 and 10% by weight, respectively, of glycerol monoalkyl ether. The preservatives of DE-40 26 756 are active against various bacteria and yeasts.

DE-C-41 40 473 discloses compositions usable as skin antiseptics and hand disinfectants, which compositions comprise a combination of an aliphatic $C_1$- to $C_6$alkylalcohol component and at least one glycerol monoalkyl ether in aqueous solution. A preferred glycerol ether is 1-(2-ethylhexyl) glycerol ether (Sensiva SC 50).

DE-A-41 24 664 describes antimicrobially active mixtures which comprise a synergistic combination of aryl-substituted alkanol with diol. Examples of diols are glycerol monoalkyl ethers.

DE-A-100 25 124 discloses formulations having a content of a combination of glycerol monoalkyl ether with aryl-substituted alcohol. A preferred aryl compound is phenoxyethanol.

SUMMARY

An object underlying the present invention is to provide a disinfectant and its method of preparation having activity towards mycobacteria, which disinfectant, in particular,
  does not attack, or does not attack markedly, materials which are used in the hospital sector and must be disinfected and
  in contact with the human skin does not have an irritating activity and does not have a degreasing activity (that is to say does not obligatorily have a high content of lower alcohols—such as ethanol or isopropanol).

DESCRIPTION OF PREFERRED EMBODIMENTS

This object is achieved by a disinfectant which comprises (a) one or more 1- or 2-($C_3$- to $C_{24}$-alkyl) glycerol ethers and (b) one or more aromatic alcohols.

Examples of inventively used glycerol monoalkyl ethers are glycerol monoalkyl ethers substituted in the 1 or 2 position (that is to say symmetrically or asymmetrically) with saturated or unsaturated, branched or unbranched alkyl such as dodecyl glycerol ether decyl glycerol ether, octyl glycerol ether, propyl glycerol ether, octadecyl glycerol ether (batyl alcohol), hexadecyl glycerol ether (chimyl alcohol) and octadecenyl glycerol ether (selachyl alcohol). Preference is given to 1-monoalkyl glycerol ethers having a saturated (branched or unbranched) $C_3$ to $C_{18}$-alkyl, particular preference is given to saturated and branched $C_6$- to $C_{12}$-alkyl. Very particular preference is given to 1-(2-ethylhexyl) glycerol ether (Sensiva® SC 50).

Aromatic alcohols are selected from aryloxyalkanols (glycol monoaryl ethers), oligoalkanol aryl ethers and arylalkanols.

Aryloxyalkanols used according to the invention have the formula AR—O—(CHR)$_n$—OH where R=independently H (for n≧2) or $C_1$- to $C_6$-alkyl, where n is an integer and is preferably 2 to 10, more preferably 2 to 6, and in particular 2 or 3. Whereas the group Ar can be a nuclear-substituted or unsubstituted aryl group, unsubstituted aryl, for example phenyl or naphthyl, is preferred. Examples of inventively used aryloxyalkanols are phenoxyethanol and phenoxypropanols. Preferred phenoxypropanols are 1-phenoxypropan-2-ol, 2-phenoxypropan-1-ol or mixtures thereof, and also 3-phenoxypropan-1-ol. Oligoalkanol aryl ethers include, for example phenoxydiethanol, phenoxytriethanol and phenoxyoligoethanol and phenoxydipropanol, phenoxy-tripropanol and phenoxyoligopropanol.

Arylalkanols used according to the invention have the formula Ar—(CHR)$_n$—OH where R=independently H or $C_1$- to $C_6$-alkyl, where n is an integer and is preferably 1 to 10, more preferably 1 to 6 and in particular 1, 2, 3 or 4. While the group Ar can be a nuclear-substituted or unsubstituted aryl group, unsubstituted aryl, e.g. phenyl or naphthyl, is preferred. Examples of arylalkanols are 3-phenylpropan-1-ol, phenylethyl alcohol, veratryl alcohol (3,4-dimethoxyphenylmethyl alcohol), benzyl alcohol and 2-methyl-1-phenyl-2-propanol.

In one embodiment, the weight ratio x of component (a) to component (b) in the inventive disinfectant is 0.15 or less, preferably 0.09 or less, more preferably 0.08 to 0.03, and in particular 0.07 to 0.04.

In a further embodiment according to the invention, the disinfectant is present in the form of a working mixture and comprises a relatively small amount of components (a) and (b), e.g. (a) 0.05 to 1% by weight of one or more glycerol monoalkyl ethers, e.g. 1-(2-ethylhexyl) glycerol ether, and (b) 0.2 to 5% by weight of one or more aromatic alcohols such as glycol monoaryl ether. One example of a working mixture is a working solution. A preferred working solution is present as an aqueous solution and comprises more than 95% by weight of water, e.g. 96 to 99.5% by weight, more preferably 97 to 99% by weight, in particular 98 to 98.5% by weight of water. Particular preference is given to a working solution which comprises (a) 0.05 to 0.2% by weight of 1-(2-ethylhexyl) glycerol ether and (b) 1.0 to 2.0% by weight of phenoxyethanol. Alternatively, the working mixture can be present in solid, pasty or high-viscosity form.

In a further embodiment of the invention the disinfectant is present as concentrate and comprises relatively high amounts of components (a) and (b). Because a preferred concentrate is a single-phase concentrate which may be formulated particularly easily with other components to give a working mixture, a preferred inventive concentrate is present in anhydrous form, because of the limited water solubility of components (a) and (b) (Sensiva SC 50 is soluble in water at room temperature up to 0.1% by weight, phenoxyethanol, for example, is soluble in water at room temperature up to 1.8% by weight).

In addition to the inventive components (a) and (b) the disinfectant can comprise other components. Preferably, however, it is low in surfactants and comprises less than 5% by weight of surfactant, preferably less than 2% by weight, particularly preferably less than 0.5% by weight of surfactant and especially preferably is surfactant free. The further components can be solid, liquid or gaseous other active compounds, functional additives or aids.

Because of the particular physiological compatibility, inventive disinfectants have a broad field of application. They can be clear, homogeneous, e.g. aqueous formulations, or can be low-viscosity or high-viscosity formulations, for example gels. The disinfectants are active over a broad pH range and are usable in strongly acidic to strongly alkaline media, preferably in the pH range from 3 to 11, particularly preferably 5 to 9.

Examples of compositions designated here as disinfectants are:
1) technical products such as biocide dispersions, dispersions in the agricultural sector, pesticide formulations, polymer dispersions, adhesives, thickeners, dyes, coating materials, pigment dispersions, photographic materials (for example developer solutions),
2) dermatological and cosmetic products, for example for topical application or as leave-on or rinse-off products such as sun protection preparations, moist cloths, polymer formulations having film-forming properties, toothpastes, care products, makeup, lipsticks, nail polish,
3) pharmaceutical preparations such as isotonic solutions, drugs and vaccines and
4) disinfectant preparations such as deodorants, foot deodorants, alcoholic spray disinfectants and compositions for manual instrument cleaning.

Surfaces with which inventive disinfectants can be treated are:
i) biological materials such as skin, mucous membrane, wounds, plants, plant parts,
ii) materials which come into contact with skin, mucous membrane or wounds, such as contact lenses or wound dressings,
iii) surfaces such as medical equipment, medical instruments (for example endoscopes) or surfaces such as floors and operation benches.

A further inventive embodiment relates to a process for treating the said surfaces, in particular for controlling mycobacteria. For this the inventive disinfectant is allowed to act on the surface to be disinfected. The inventive disinfection process is used in particular in the disinfection of medical instruments or laboratory equipment, in which case the surfaces to be disinfected can be fabricated from metal, glass, plastic or ceramics.

The inventive disinfection process can be reinforced by ultrasound, pressure or microwave radiation. Those skilled in the art will select here an optimum between the parameters time of action and concentration of the components (a) and (b) which corresponds to the desired microbicidal action, depending on the sensitivity of the material to be disinfected.

The inventive disinfectants can have activity towards bacteria (Gram-positive) and (Gram-negative), yeasts and moulds, mycobacteria and viruses. Thus, they are, for example, active towards propionibacteria (*Propionibacterium acnes*), dandruff-causing microorganisms, prions, antibiotic-resistant microorganisms, enveloped and/or nonenveloped viruses, odour-causing microorganisms, lower pathogens, protozoa and spores.

The present invention offers, inter alia, the following advantages:
  The disinfectants can be formulated from inexpensive components.

The disinfectants are pH neutral, scarcely aggressive (low corrosion) and correspondingly readily material-compatible.

The agents are low-odour, low-emission, inert and readily compatible with other additives or aids, toxicologically and ecotoxicologically harmless, physiologically harmless (good skin compatibility), of high keeping quality and easily washed off.

The agents show no tendency to discoloration, are active in short times of action and, owing to the synergistic increase in activity, require a low concentration of active compound.

The agents are low-foaming and oxidation- and pH-stable.

The advantages of the invention are given in particular by the following examples.

EXAMPLES

The following abbreviations are used:

| | |
|---|---|
| SC 50 | 1-(2-ethylhexyl) glycerol ether Sensiva SC 50 |
| Water | demineralized water |
| Ethanol | ethanol, denatured with methyl ethyl ketone |
| POE | phenoxyethanol |

Unless explicitly stated otherwise, all percentages are percent by weight.

Example 1

Activity of Disinfectants Towards *Mycobacterium terrae* at Room Temperature

Various aqueous disinfectants were tested with respect to their activity towards *Mycobacterium terrae*, cell count 1 to $3 \times 10^9$ in a quantitative suspension test without load. The following reduction factors were measured, a reduction factor>5 corresponding to a sufficient Tb activity. For this various amounts of ethanol were added to aqueous active compound solutions and after exposure for 15, 30 and 60 minutes were tested. For testing the tuberculocidal activity, the quantitative suspension test *Mycobacterium terrae* (ATCC15755) was used in accordance with the Deutsche Gesellscaft für Hygiene and Mikrobiologie [German Society for Hygiene and Microbiology] of 30 Apr. 1997 (Hyg. Med. 22, 1997, issue 6, pages 278ff.).

Result:

Tests with *Mycobacterium tuberculosis* were not carried out because of the hazardousness of the tuberculosis bacterium. Owing to the strong structural similarity of *Mycobacterium terrae* with *Mycobacterium tuberculosis*, however, the results above permit the activity tests with *Mycobacterium terrae* to provide information on the activity towards *Mycobacterium tuberculosis*.

Aqueous ethanol, even at a content of 30%, is not sufficiently Tb active. By adding 0.1% glycerol monoalkyl ether Sensiva SC 50, 30% strength ethanol is sufficiently Tb active at an exposure time of 60 minutes. By adding 1.5% glycol monoaryl ether POE, 20% ethanol at an exposure time of 30 minutes is sufficiently Tb active. In contrast, an inventive combination of 0.1% Sensiva SC 50 with 1.5% POE is Tb active at room temperature at an exposure time of 30 minutes even without ethanol addition.

Inventive aqueous working solutions are sufficiently active even at low contents of components (a) and (b). In addition, inventive compositions, for activity towards mycobacteria, do not require a comparatively high amount of ethanol which is undesirable, inter alia, because of the associated corrosive action towards various materials and the extractive action in the case of exposure to hands, for example.

Example 2

Activity of Disinfectants in the Koko Test

The following aqueous working solutions were examined using Ringer solution as product in the Koko test:

Analytical Principle

Using the method described, the activity of chemical preservatives is tested with respect to package preservation for cosmetics formulations. For this, in various experimental batches, the preservatives under test at various concentrations are added to the non-preserved samples. A continuous microbial load is achieved by periodic inoculation of the experimental batches. In parallel to the inoculation, in each case immediately before, streak samples of the individual batches were taken. Evaluation is made on the basis of microbial growth of the streak samples. A preservative is more effective, the longer the period to the first appearance of microbial growth.

Solutions and Nutrient Media
  CSA (caseine peptone—soya bean peptone agar)
  SA (Sabouraud dextrose agar)
  SA slope tubes
  CSA+TLSH (No. 4)
  SA-TLSH (No. 10)
  NaCl (physiological common salt solution, 8.5%)

| Comp. | Comp. without ethanol content | | | 10% EtOH | | | 20% EtOH | | | 30% EtOH | | |
|---|---|---|---|---|---|---|---|---|---|---|---|---|
| | 15' | 30' | 60' | 15' | 30' | 60' | 15' | 30' | 60' | 15' | 30' | 60' |
| A | 0 | 0 | 0 | 0 | 0 | 0 | 0 | 0 | 0 | 0.83 | 2.78 | 4.65 |
| B | 0 | 0 | 0 | 0 | 0 | 0 | 0 | 0 | 0.66 | 2.02 | 4.02 | 5.52 |
| C | 0 | 0 | 0 | 0 | 1.92 | 2.98 | 3.67 | 6.14 | 5.36 | 5.49 | 6.14 | 5.36 |
| D | 2.94 | 5.41 | 5.52 | 4.66 | 5.41 | 5.52 | 5.36 | 5.41 | 5.52 | 5.36 | 5.41 | 5.52 |

A) water
B) 0.1% SC 50 in water
C) 1.5% POE in water
D) 0.1% SC 50 + 1.5% POE in water The test organism used was the mixed suspension (group 5) of the following four test organism groups.

| Group 1 (Koko 1) | Staphylococcus aureus | ATCC 6538 |
|---|---|---|
| | Staphylococcus epidermis | ATCC 12228 |
| Group 2 (Koko 2) | Enterobacter gergoviae | Dr Eigner/Beiersdorf company 1994 |
| | Escherichia coli | ATCC 11229 |
| | Klebsiella pneumoniae | ATCC 4532 |
| Group 3 (Koko 3) | Pseudomonas aeruginosa | ATCC 15442 |
| | Pseudomonas fluorescens | ATCC 17397 |
| | Pseudomonas purida | ATCC 12633 |
| Group 4 (Koko 4) | Aspergillus niger | ATCC 6275 |
| | Penicillium funicolosum | ATCC 36839 |
| | Candida albicans | ATCC 10231 |

Growth of Test Organisms
Bacteria: streak with sterile glass rod on CS agar
Yeasts: streak with sterile glass rod on SA agar
Fungi: *Aspergillus niger* is transferred to 4Sa-slope
  *Penicillium* funiculosum is transferred to Sa agar plates
  All test organisms are incubated for one week at 25° C.±2° C. The test organisms are renewed at intervals of 3 to 4 months.
Preparation of the Inoculation Solution (Groups 1 to 3)
  The bacteria are suspended in each case with 5 ml of NaCl solution, filtered through a glass funnel containing glass wool into a 100 ml measuring cylinder and made up to 100 ml with NaCl. The bacterial suspensions have a titre of approximately $10^9$ CFU/ml.
Preparation of the Inoculation Solution (Group 4)
  Three *Aspergillus niger* slope tubes are shaken each with 3 ml of NaCl solution on the Heldolph stirrer and passed through a glass funnel containing glass wool. The yeast *Candida albicans* is suspended with 5 ml of NaCl and also poured through the glass funnel. 5 ml of a *Penicillium funiculosum* suspension (see analytical procedure No. 22 for preparation of the fungal suspension) is added to this mixture and the mixture is made up to 100 ml with NaCl. The fungal suspension has a titre of approximately $10^{5-9}$ CFU/ml.
Preparation of the Inoculation Solution (Group 5)
  The inoculation solution actually used is prepared as described above (groups 1 to 4). After the suspension this is mixed and only then made up to 100 ml with NaCl.
  The microbial suspensions are transferred to sterile glass-stoppered flasks containing glass beads and shaken for 5 min at a shaking frequency of 200 units/minute (to-and-fro motion). The microbial content of the mixed suspensions is at around $10^9$ CFU/ml. The suspension should be used on the day of preparation, but if stored in a refrigerator, can also be used after 24 hours.
Procedure
  In separate batches, in each case 25 g of the cosmetic under test is admixed with the preservatives under test at differing concentrations. A non-preserved product sample serves in each case as growth control. The test batches are streaked onto CSA/TLSH and Sa/TLSH using a sterile glass rod after thorough stirring once a week, the first streak being carried out immediately before the new inoculation. All samples are inoculated with 0.1 ml of the respective microbial suspension and stirred thoroughly.
  The microbial growth of the streak samples is evaluated after incubation for three days at 25° C.±2° C. Negative streak samples, for a safety margin, are observed for a further 2 days and again evaluated. The preservative activity of the individual product concentration is evaluated in semiquantitative method via growth of the individual streak samples.

The test is usually carried out over six inoculation cycles and interrupted after solid overgrowth has occurred twice.
Evaluation of the Results
  A preservative is to be considered good if, under the laboratory conditions above, there is a period of 6 weeks without microbial infection of the test batches, that is to say even after the sixth inoculation no microbial growth is detectable.

| | Inoculation cycles withstood |
|---|---|
| 0.1% SC 50 | 0 |
| 1.0% POE | 1 |
| 0.1% SC 50 + 1.0% POE | >6 |

Result:
  Inventive disinfectants show in the Koko test a synergistic action of components (a) and (h).

Example 3

Increase in Activity of Inventive Disinfectants Towards *B. subtilis* by Addition of $H_2O_2$ The following disinfectants were formulated:

| | 3A | 3B | 3C | 3D | 3E | 3F |
|---|---|---|---|---|---|---|
| SC 50 | 0.1 | 0.1 | 0.1 | 0.1 | | 0.1 |
| POE | 1.5 | 1.56 | 1.5 | 1.5 | | 1.5 |
| $H_2O_2$ 30% | 16.7 | 13.3 | 10.0 | 6.7 | 16.7 | |
| Water | 81.7 | 85.1 | 88.4 | 91.7 | 83.3 | 98.4 |

With these disinfectants, the following reduction factors were obtained with *B. subtilis*. In this case the procedure is carried out on the basis of DIN draft EN14347 "sporicidal action (base test)" of February 2002, see, in particular, point 5.5.2.2.1 there.

| Comp. | Dilution with water | Exposure time | | | | | | % $H_2O_2$ A.I. |
|---|---|---|---|---|---|---|---|---|
| | | 15' | 30' | 60' | 2 h | 4 h | 6 h | |
| 3A | not diluted | 0.22 | 0.29 | 0.45 | 0.54 | 4.70 | 4.78 | 5% |
| 3B | not diluted | 0.14 | 0.15 | 0.25 | 0.50 | 0.81 | 4.78 | 4% |
| 3C | not diluted | 0.23 | 0.20 | 0.31 | 0.47 | 0.51 | 2.99 | 3% |
| 3D | not diluted | 0.28 | 0.26 | 0.34 | 0.41 | 0.42 | 0.76 | 2% |
| 3E | not diluted | 0.29 | 0.30 | 0.40 | 0.49 | 1.66 | 4.78 | 5% |
| 3F | not diluted | 0 | 0 | 0 | 0 | 0.37 | 0.19 | |

Result:
  The spore activity of inventive disinfectants can be increased by adding $H_2O_2$.

Example 4

Activity of Disinfectants Towards Bacteria and Yeast Fungi

The following three formulations were examined with respect to their activity:

| | | |
|---|---|---|
| 4A | 0.1% SC 50 in water | |
| 4B | 1.5% POE in water | |
| 4C | 0.1% SC 50 + 1.5% POE in water | |

Using these formulations the following reduction factors were obtained (SA=*Staphylococcus aureus*, PS=*Pseudomonas aeruginosa*, EC=*Escherichia coli*, PM=*Proteus merabilis* and CA=*Candida albicans*), in which case 50% and 25% dilutions with water were also studied (initial cell count $0.8-5\times10^9$/ml, at CA $2\times10^7$/ml, deinhibition Tryp-NaCL-TLSH (No. 22).

Method:

0.1 ml of the microbial suspension in CSL is mixed thoroughly at room temperature with 10 ml of the disinfectant dilution under test (in water of standardized hardness, WSH). After exposure times of 5, 15, 30 and 60 minutes, in each case 1 ml is taken off from the disinfectant/microbial mixture and inoculated into 9 ml of inactivation liquid (0.1% tryptone+ 0.85% NaCl in twice-distilled water+inactivation substances). After at most 30 minutes contact time in inactivation liquid, dilutions ($10^{-2}$ and $10^{-4}$ in 0.1% tryptone+0.85% NaCl in twice-distilled water) are made up. Then, 0.1 ml each of the inactivation liquid and the two dilutions are spread onto 3 CSA plates each. As a control the respective solid microbial suspension is mixed with 10 ml of WSH, instead of disinfectant. In parallel to the corresponding exposure times, subcultures are to be made up from this batch in the same manner.

All subcultures are incubated for 48 hours at 37° C., in the case of *Candida albicans* for 72 hours at 37° C., and the colonies are counted. The reduction is calculated in the following manner: KWEs between 20 and 300 per CSA plate are to evaluated. After determining the arithmetic mean of three values, the disinfectant action ($KR_t$) per unit time is calculated from the formula $KR_t = \log_{CFU(co)}$ minus $\text{logarithm}_{CFU(D)}$, where (CFU(co) is the number of CFUs per ml without action of the preparation and CFU(D) is the number of CFUs per ml after action of the preparation.

| | Starting concentration | 5' | 15' | 30' | 60' | 5' | 15' | 30' | 60' |
|---|---|---|---|---|---|---|---|---|---|
| | | | SA | | | | PS | | |
| 4A | 100% | 0 | 0 | 0 | 0 | 0 | 0 | 0 | 0 |
| | 50% | 0 | 0 | 0 | 0 | 0 | 0 | 0 | 0 |
| | 25% | 0 | 0 | 0 | 0 | 0 | 0 | 0 | 0 |
| | | | EC | | | | PM | | |
| | 100% | 0 | 0 | 0 | 0 | 0 | 0 | 0 | 0 |
| | 50% | 0 | 0 | 0 | 0 | 0 | 0 | 0 | 0 |
| | 25% | 0 | 0 | 0 | 0 | 0 | 0 | 0 | 0 |
| | | | CA | | | | | | |
| | 100% | 0 | 0.59 | 0.05 | 0.22 | | | | |
| | 50% | 0 | 0.41 | 0.07 | 0 | | | | |
| | 25% | 0 | 0.19 | 0 | 0 | | | | |
| | | | SA | | | | PS | | |
| 4B | 100% | 0 | 0 | 0 | 1.12 | 1.74 | 5.38 | 5.26 | 5.46 |
| | 50% | 0 | 0 | 0 | 0 | 0 | 0 | 0 | 0 |
| | 25% | 0 | 0 | 0 | 0 | 0 | 0 | 0 | 0 |
| | | | EC | | | | PM | | |
| | 100% | 2.53 | 4.70 | 5.15 | 5.15 | 5.04 | 4.90 | 5.18 | 5.11 |
| | 50% | 0 | 0 | 0 | 0 | 0 | 0 | 0 | 0 |
| | 25% | 0 | 0 | 0 | 0 | 0 | 0 | 0 | 0 |
| | | | CA | | | | | | |
| | 100% | 0.43 | 0.45 | 0.35 | 0.33 | | | | |
| | 50% | 0.13 | 0.38 | 0.35 | 0.33 | | | | |
| | 25% | 0 | 0.29 | 0.35 | 0.22 | | | | |
| | | | SA | | | | PS | | |
| 4C | 100% | 3.30 | 3.55 | 4.20 | 4.70 | 5.81 | 5.38 | 5.26 | 5.46 |
| | 50% | 0 | 0 | 0 | 0 | 0 | 0 | 0 | 0 |
| | 25% | 0 | 0 | 0 | 0 | 0 | 0 | 0 | 0 |
| | | | EC | | | | PM | | |
| | 100% | 5.00 | 4.70 | 5.15 | 5.15 | 5.04 | 4.90 | 5.18 | 5.11 |
| | 50% | 0 | 0 | 0 | 0 | 0 | 0 | 0 | 0 |
| | 25% | 0 | 0 | 0 | 0 | 0 | 0 | 0 | 0 |
| | | | CA | | | | | | |
| | 100% | 1.85 | 3.49 | 3.30 | 3.18 | | | | |
| | 50% | 0.07 | 0.13 | 0.35 | 1.18 | | | | |
| | 25% | 0.16 | 0 | 0.52 | 0.27 | | | | |

Result: these data show a partial synergistic action of the combination of SC 50 with POE.

Example 5

Activity of Disinfectants Towards *Micrococcus luteus* in the Skin Test

The following ethanol-containing disinfectants were formulated. The test method used was the "Richtlinie für die Prüfung und die Bewertung von Hautdesinfektionsmitteln" [Guideline for testing and evaluation of skin disinfectants] of the Deutsche Gesellschaft für Hygiene und Mikrobiologie of 1 Jan. 1991, see Zbl. Hyg. 192, pages 99-103 (1991).

| | 5A | 5B | 5C | 5D | 5E* |
|---|---|---|---|---|---|
| Ethanol | 35.0 | 35.0 | 35.0 | 35.0 | |
| SC 50 | | 1.0 | | 0.5 | |
| POE | | | 1.0 | 0.5 | |
| Water | 65.0 | 64.0 | 64.0 | 64.0 | 30 |
| Isopropanol | | | | | 70 |

*reference solution as in DGHM guidelines for testing and evaluation of skin disinfectants The following reduction factors were obtained:

| Exposure time | | | | | |
|---|---|---|---|---|---|
| 30 seconds | 0.68 | 2.36 | 1.55 | 2.83 | 2.11 |
| 1 minute | 0.75 | 2.86 | 1.95 | 3.21 | 2.30 |
| 2 minutes | 1.25 | 3.35 | 1.77 | 3.66 | 2.37 |

Result:

Compared with the reference solution, the inventive composition shows an improved activity, the inventive working solution (5D) comprising 64% or water, compared with the reference solution comprising only 30% water. The inventive formulation is thus much more compatible for the skin. From the comparison with the formulation 5B not according to the invention, it was found that by combination with POE, a portion of the comparatively expensive SC 50 can be replaced and this combination even results in an improvement in activity.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A concentrate comprising:
   (a) 1-(2-ethylhexyl) glycerol ether; and
   (b) one or more aromatic alcohols,
   (a) and (b) having a weight ratio of (a)/(b) is less than or equal to 0.15,
   wherein the concentrate is in anhydrous form.

* * * * *